(12) United States Patent
Holmeide

(10) Patent No.: US 8,741,966 B2
(45) Date of Patent: Jun. 3, 2014

(54) LIPID COMPOUNDS FOR USE IN COSMETIC PRODUCTS, AS FOOD SUPPLEMENT OR AS A MEDICAMENT

(75) Inventor: Anne Kristin Holmeide, Oslo (NO)

(73) Assignee: Pronova Biopharma Norge AS, Baerum (NO)

( * ) Notice: Subject to any disclaimer, the term of this patent is extended or adjusted under 35 U.S.C. 154(b) by 468 days.

(21) Appl. No.: 12/741,890

(22) PCT Filed: Nov. 6, 2008

(86) PCT No.: PCT/NO2008/000391
§ 371 (c)(1),
(2), (4) Date: Jul. 27, 2010

(87) PCT Pub. No.: WO2009/061208
PCT Pub. Date: May 14, 2009

(65) Prior Publication Data
US 2010/0280109 A1   Nov. 4, 2010

Related U.S. Application Data

(60) Provisional application No. 60/986,698, filed on Nov. 9, 2007.

(51) Int. Cl.
| A61K 31/095 | (2006.01) |
| A61K 31/10 | (2006.01) |
| A61K 31/21 | (2006.01) |
| C07C 317/08 | (2006.01) |
| C07C 69/52 | (2006.01) |
| C07C 321/18 | (2006.01) |
| C07C 303/00 | (2006.01) |

(52) U.S. Cl.
USPC ........... 514/706; 514/708; 514/709; 514/712; 514/713; 514/506; 560/150; 560/222; 560/147; 560/149; 560/266; 554/42; 554/44

(58) Field of Classification Search
None
See application file for complete search history.

(56) References Cited

U.S. PATENT DOCUMENTS

| 2,909,554 A | 10/1959 | Doerr |
| 4,009,211 A | 2/1977 | Onopchenko et al. |
| 4,032,564 A | 6/1977 | Henrick et al. |
| 4,040,781 A | 8/1977 | Lamberti et al. |
| 4,209,410 A | 6/1980 | Baldwin |
| 4,214,088 A | 7/1980 | Abeler et al. |
| 4,286,053 A | 8/1981 | Ishikawa et al. |
| 4,297,268 A | 10/1981 | Abeler et al. |
| 4,368,190 A | 1/1983 | Shen et al. |
| 4,411,808 A | 10/1983 | Gutierrez et al. |
| 4,444,766 A | 4/1984 | Bosies et al. |
| 5,306,754 A | 4/1994 | Yamamoto et al. |
| 5,328,953 A | 7/1994 | Lynch |
| 5,447,820 A | 9/1995 | Hayakawa et al. |
| 5,612,093 A | 3/1997 | Braig et al. |
| 5,763,517 A | 6/1998 | Yamamoto et al. |
| 5,770,584 A * | 6/1998 | Kucera et al. ................. 514/77 |
| 5,990,173 A | 11/1999 | Patoiseau et al. |
| 6,060,515 A | 5/2000 | Elias et al. |
| 6,511,670 B1 | 1/2003 | Maignan et al. |
| 6,624,190 B2 | 9/2003 | Khoury et al. |
| 6,723,717 B1 | 4/2004 | Youngquist et al. |
| 7,250,456 B2 | 7/2007 | Eigen et al. |
| 7,273,852 B2 | 9/2007 | Tsuji et al. |
| 7,427,583 B2 | 9/2008 | Couillet et al. |
| 7,517,858 B1 * | 4/2009 | Hostetler et al. ................. 514/23 |

(Continued)

FOREIGN PATENT DOCUMENTS

| CA | 2115345 | 2/1993 |
| CN | 101225064 | 7/2008 |

(Continued)

OTHER PUBLICATIONS

Meyer, K. L., et al., In vitro evaluation of phosphocholine and quaternary ammonium containing lipids as novel anti-HIV agents, 1991, J. Med. Chem, vol. 34, No. 4, pp. 1377-1383.*

(Continued)

Primary Examiner — Yate K Cutliff
(74) Attorney, Agent, or Firm — Finnegan, Henderson, Farabow, Garrett & Dunner LLP

(57) ABSTRACT

The present disclosure relates to lipid compounds of formula (I):

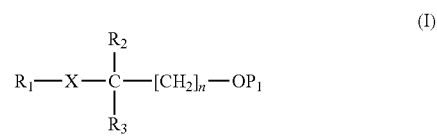

wherein:
R$_1$ is chosen from a C$_{10}$-C$_{21}$ alkyl, a C$_{10}$-C$_{21}$ alkenyl having 1-6 double bonds, and a C$_{10}$-C$_{21}$ alkynyl having 1-6 triple bonds;
R$_2$ and R$_3$ are the same or different and are chosen from hydrogen and a C$_1$-C$_6$ alkyl;
X is chosen from O, S, SO, SO$_2$, Si, and Se;
n=1 or 3; and
P$_1$ is chosen from hydrogen; a C$_{10}$-C$_{21}$ alkyl, a C$_{10}$-C$_{21}$ alkenyl having 1-6 double bonds, a C$_{10}$-C$_{21}$ alkynyl having 1-6 triple bonds, optionally substituted; a group of formula (II) or formula (III), wherein P$_2$, P$_3$, and P$_4$ are chosen from hydrogen, an alkyl, an alkenyl, and an alkynyl, optionally substituted; and a group of formula (IV) or formula (V), wherein P$_5$ is chosen from hydrogen and a C$_1$-C$_6$ alkyl;
or a pharmaceutically acceptable salt, complex, or solvate thereof. Also disclosed are pharmaceutical compositions and lipid compositions comprising such compounds, and methods of use thereof, for example in the treatment of diseases related to cardiovascular, metabolic, and inflammatory conditions.

48 Claims, No Drawings

(56) References Cited

U.S. PATENT DOCUMENTS

| | | | |
|---|---|---|---|
| 7,902,399 | B2 | 3/2011 | Berge et al. |
| 7,968,617 | B2 | 6/2011 | Thalacker et al. |
| 8,304,551 | B2 | 11/2012 | Milne et al. |
| 2003/0147814 | A1 | 8/2003 | Scherrer et al. |
| 2004/0126424 | A1 | 7/2004 | Jandacek et al. |
| 2005/0107503 | A1 | 5/2005 | Couillet et al. |
| 2006/0135785 | A1 | 6/2006 | Patoiseau et al. |
| 2006/0247458 | A1 | 11/2006 | Yamamoto et al. |
| 2007/0060497 | A1 | 3/2007 | Krahmer et al. |
| 2007/0167529 | A1* | 7/2007 | Walton et al. ............ 514/721 |
| 2007/0254862 | A1 | 11/2007 | Antel et al. |
| 2009/0137567 | A1 | 5/2009 | Perrine et al. |
| 2011/0190395 | A1 | 8/2011 | Holmeide et al. |
| 2012/0122940 | A1 | 5/2012 | Hovland et al. |
| 2012/0252850 | A1 | 10/2012 | Milne et al. |
| 2012/0264791 | A1 | 10/2012 | Milne et al. |
| 2013/0046013 | A1 | 2/2013 | Hovland et al. |

FOREIGN PATENT DOCUMENTS

| | | | |
|---|---|---|---|
| EP | 0002007 | | 5/1979 |
| EP | 0002007 A1 | | 5/1979 |
| EP | 0050327 | | 4/1982 |
| EP | 0050327 A1 | | 4/1982 |
| EP | 0 175 591 | | 3/1986 |
| EP | 0175591 | | 3/1986 |
| EP | 0399183 | | 11/1990 |
| EP | 0463947 | | 1/1992 |
| EP | 0463947 A1 | | 1/1992 |
| GB | 1038723 | | 8/1966 |
| GB | 1038723 A | | 8/1966 |
| GB | 1523276 | * 8/1978 | ............ C07C 149/24 |
| JP | 04-051149 | | 2/1992 |
| JP | 11180929 | * 7/1999 | ............. C07C 59/60 |
| WO | WO97/38688 | | 10/1997 |
| WO | WO00/72920 | | 12/2000 |
| WO | WO01/98328 | | 12/2001 |
| WO | WO 01/98328 A2 | | 12/2001 |
| WO | WO03/014073 | | 2/2003 |
| WO | WO2005/073164 | | 8/2005 |
| WO | WO2006/025246 | | 3/2006 |
| WO | WO 2006/025246 A1 | | 3/2006 |
| WO | WO2006/094915 | | 9/2006 |
| WO | Wo 2006/117664 | | 11/2006 |
| WO | WO 2006/117668 | | 11/2006 |
| WO | WO2007/116027 | | 10/2007 |
| WO | WO2008/053331 | | 5/2008 |
| WO | WO 2008/053331 A1 | | 5/2008 |
| WO | WO2008/053340 | | 5/2008 |
| WO | WO2008/125241 | | 10/2008 |
| WO | WO2009/061208 | | 5/2009 |
| WO | WO2009/149496 | | 12/2009 |
| WO | WO2009/156621 | | 12/2009 |
| WO | WO2010/006085 | | 1/2010 |
| WO | WO2010/008299 | | 1/2010 |
| WO | WO2010/128401 | | 11/2010 |
| WO | WO2011/089529 | | 7/2011 |
| WO | WO2012/059818 | | 5/2012 |
| WO | WO2012/115695 | | 8/2012 |
| WO | WO2013/016531 | | 1/2013 |

OTHER PUBLICATIONS

Tsotinis, A. et al., Synthesis of Antiretroviral evaluatin of new alkoxy and aryloxy phosphate derivatives of 3'-azido-3'—deoxythymidine, 1996, J. Med. Chem., vol. 39, No. 17, pp. 3418-3422.*
Togashi, N., et al., Antibacterial activity of long-chain fatty alcohols atains *Staphylococcus aureus*, Feb. 20007, Molecules, pp. 139-148.*
Nystrom R.F., et al. Reducitn of organic compounds by lithium aluminum hydrode. II. carboxylic acids, 1947, Contribution from the George Herbert Jones laboratory, the University of Chicago, vo. 69, pp. 2548-2549.*
Stahl, P.H., et al., Handbook of pharmaceutical salts, 2008, Verlag Helvetica Chimica Acta, 33 pages.*
Berge, S.M., Pharmaceutical Salts, 1977, Journal of Pharmaceutical Sciences, vol. 66, No. 1, 19 pages.*
Silverman, R.B., The organic chemistry of druge design and drug action, 1992, Academic press, 20 pages.*
Ahmad, J. et al., "Reactions in monolayers: Base-catalyzed ester hydrolysis revisited," *Langmuir* (1990) vol. 6, pp. 1797-1799.
English abstract of EP 0463947 A1 (1 page), 1992.
Ferrell, W.J., "Synthesis and properties of 35S, 14C and 3H labeled S-alkyl glycerol ethers and derivatives," *Chemistry and Physics of Lipids* (1976) vol. 16, pp. 276-284.
Goldsworthy, L.J. et al., "Some sulfides containing the 2-chloroethyl group," *J. Chem. Soc.* (1948) Part II, pp. 2177-2179.
International Search Report of PCT/NO2008/000391 dated Feb. 4, 2009. (12 pages).
Livingston, J.R. et al., "The synthesis and some surface active properties of alkylthioalkyl and alkoxyalkyl sulfates," *J. Am. Oil. Chem. Soc.* (1965) vol. 42, pp. 720-723.
Okoronkwo, A.E. et al., "Synthesis of w-hydroxy-a-alkyl/aryl-g-organo-selenium and g-organo-tellurium: A new class of organochalcogen compounds with antinociceptive activity," *Tetrahedron Letters* (2008) vol. 49, pp. 3252-3256.
Registry Copyright 2008 ACS on STN (RN 785712-42-7, 714185-72-5, 45247-37-8).
Shirley, D.A. et al., "Alkylation with long chain p-toluenesulfonates. IV. 1 Alkylation of alcohols and amines with n-octadecyl p-toluenesulfonate," *J. Org. Chem.* (1953) vol. 18, pp. 378-381.
STN International CAPLUS accession No. 1982:509519, Doc. No. 97:109519: Derzhinskii A.R. et al., "Functional sulfur-containing compounds. Part 4. Synthesis of chloro(bromo)alkyl sulfones by oxidative halogenations of hydroxyalkyl sulfides and sulfoxides using a hydrogen peroxide-halogen acid mixture," Izvestiya Akademii Nauk SSSR, Seriya Khimicheskaya (1982), vol. 5, pp. 1116-1123.
STN International CAPLUS accession No. 1966:69067, Doc. No. 64:69067: Kasai, Y. et al., "The preparations and the surface activities of salts of diphenylalkanesulfonic acids," Kogyo Kagaku Zasshi (1965) vol. 68, pp. 2073-2077.
Zeinalov, B.K., "Synthesis and study of alkylselenoethanol esters," *Azerbaidzhanskii Khimicheskii Zhumal* (1981) vol. 5, pp. 41-43.
Ahmad et al., "Reactions in monolayers: base-catalyzed ester hydrolysis revisited," 6 *Langmuir* 1797-1799 (1990).
Co-pending U.S. Appl. No. 13/054,212, filed Apr. 13, 2011, continuation of PCT/NO2009/000262.
Co-pending U.S. Appl. No. 13/319,101, filed Jan. 24, 2012, continuation of PCT/IB2010/01251.
Co-pending U.S. Appl. No. 13/574,132, filed Jul. 19, 2012, continuation of PCT/IB2011/00250.
Co-pending U.S. Appl. No. 13/883,405, filed May 3, 2013, continuation of PCT/IB2011/002925.
Derzhinskii et al., "Functional sulfur-containing compounds. Part 4. Synthesis of chloro(bromo)alkyl sulfones by oxidative halogenation of hydroxyalkyl sulfides and sulfoxides usinga hydrogen peroxide-halogen acid mixture," 5 *Izvestiya Akademii Nauk SSSR Seriya Khimicheskaya* 995-1001 (1982) (English translation).
English language abstract for CN101225064.
English language abstract for EP0463947.
English language abstract for JP04-051149.
Ferrell, William J., "Synthesis and properties of 35S, 14C and 3H labeled S-alkyl glycerol ethers and derivatives," 16 *Chemistry and Physics of Lipids* 276-284 (1976).
Ferruccci et al., "Relationship of plasma polyunsaturated fatty acids to circulating inflammatory markers," 91(2) *J. Clin. Endocrin. Metab.* 439-446 (2006).
Flock et al., "Syntheses of some polyunsaturated sulfur- and oxygen-containing fatty acids related to eicosapentaenoic and docosahexaenoic acids," 53 *Acta Chemica Scandinavica* 436-445 (1999).
Geleijnse et al., "Blood pressure response to fish oil supplementation: metaregression analysis of randomized trials," 20 *J. Hypertension* 1493-1499 (2002).
Goldsworthy et al., "Some sulfides containing the 2-chloroethyl group," *Journal of the Chemical Society* 2177-2179 (1948).

(56) References Cited

OTHER PUBLICATIONS

Goodman et al., "Drugs effective in the therapy of the epilepsies," *Basis of Therapeutics* 201-26 (5$^{th}$ Ed. 1975).
Grupp et al., "Protection against Hypoxia-reoxygenation in the absence of poly(ADP-ribose) synthetase in isolated working hearts," 31 *J. Mol Cell Cardiol.* 297-303 (1999).
Haraldsson, "Marine lipids for prodrugs, soft compounds and other pharmaceutical applications," 55 *Pharmazie* 3 172-177 (2000).
Hermetter, "A facile procedure for the synthesis of saturated phosphatidylcholines," 28 *Chemistry and Physics of Lipids* 111-115 (1981).
Holmeide et al., "Syntheses of some polyunsaturated trifluoromethyl ketones as potential phospholipase A2 inhibitors," 1 *J. Chem. Soc., Perkin Trans.* 2271-2276 (2000).
Hosokawa et al., "Preparation of therapeutic phospholipids through porcine pancreatic phospholipase As-mediated esterification and lipozyme-mediated acidolysis," 72 *J. Am. Oil Chem. Soc.* 1287-1291 (1995).
International Search Report for International Application No. PCT/IB2010/001251, dated Oct. 4, 2010.
International Search Report for International Application No. PCT/IB2011/000250, dated May 31, 2011.
International Search Report for International Application No. PCT/IB2011/002925, dated Mar. 5, 2012.
International Search Report for International Application No. PCT/NO2008/000391, dated Feb. 4, 2009.
International Search Report for International Application No. PCT/NO2009/000262, dated Oct. 23, 2009.
Jones et al., "A new class of antituberculosis agents," 43 *J. Med. Chem.* 3304-3314 (2003).
Lamango et al., "Inhibition mechanism of S-adenosylmethionine-induced movement deficits by prenylcysteine analogs," 43 *Pharmacology, Biochemistry, and Behavior* 433-442 (2003).
Larsen et al., "Sulfur substituted and alpha-methylated fatty acids as peroxisome proliferator-activited receptor activators," 40 *Lipids* 49-57 (2005).
Larsen et al., "α- and β- alkyl-substituted eicosapentaenoic acids: incorporation into phospholipids and effects on prostaglandin H synthase and 5-lipoxygenase," 55 *Biochemical Pharmacology* 405-22 (1998).
Lilja-Hallberg, "Enzymatic esterification of long polyunsaturated fatty acids and lyso-phosphatidylcholine in isooctane and ethanol," 9 *Biocatalysis* 195-207 (1994).
Livingston et al., "The synthesis and some surface active properties of alkylthioalkyl and alkoxyalkyl sulfates," 42 *The Journal of the American Oil Chemists' Society* 720-723 (1965).
Office Action dated Apr. 1, 2013, in co-pending U.S. Appl. No. 13/054,212.
Office Action dated Apr. 24, 2013, in co-pending U.S. Appl. No. 13/319,101.
Office Action dated Jan. 31, 2013, in co-pending U.S. Appl. No. 13/319,101.
Okoronkwo et al., Synthesis of ω-hydroxy-α-alkyl/aryl-γ-organoselenium and γ-organo-tellurium: a new class of organochalcogen compounds with antinociceptive activity, 49 *Tetrahedron Letters* 3252-3256 (2008).
Parkkari et al., "α-methylated derivatives of 2-arachidonoyl glycerol: synthesis, CB1 receptor activity, and enzymatic stability," 16 *Bioorg. Med. Chem. Lett.* 2437-2440 (2006).
Pitt et al., "Synthesis of polyunsaturated β-oxa fatty acids via rhodium mediated carbenoid insertion," *Synthesis* 1240-42 (1997).
Registry Copyright 2008 ACS on STN.
Rossmeisl et al., "Prevention and reversal of obesity and glucose intolerance in mice by DHA derivatives," 17 *Obesity* 1023-1031 (2009).
Shirley et al., "Alkylation with long chain p-toluenesulfonates. IV.1 Alkylation of alcohols and amines with n-octadecyl p-toluenesulfonate," 18 *Journal of Organic Chemistry* 378-381 (1953).
Simonopoulos, "Essential fatty acids in health and chronic disease," 70(Suppl) *Am. J. Clin. Nutr.* 560S-569S (1999).
Srisiri et al., "Syntheses of polymerizable monoacylglycerols and 1,2-diacyl-sn-glycerols," 61 *J. Org. Chem.* 5911-5915 (1996).
Storlien et al., "Polyunsaturated fatty acids, membrane function and metabolic diseases such as diabetes and obesity," 1 *Curr. Opin. Clin. Nutr. Metab. Care* 559-563 (1998).
Tran et al., Inhibition of interleukin-1β-induced COX-2 and EP3 gene expression by sodium salicylate enhances pancreatic islet β-cell function, 51 *Diabetes* 1772-78 (2002).
Vaagenes et al., "Methylated eicosapentaenoic acid and tetradecylathioacetic acid: effects on fatty acid metabolism," 58 *Biochem. Pharmacol.* 1133-1143 (1999).
Wang et al., "Synthesis of phospholipid-inhibitor conjugates by enzymatic transphosphatidylation with phospholipase D," 115 *J. Am. Chem. Soc.* 10487-10491 (1993).
Willumsen et al., "On the effect of 2-deuterium- and 2-methyl-eicosapentaenoic acid derivatives on triglyerides, peroxisomal beta-oxidation and platelet aggregation in rats," 1369 *Biochimica et Biophysica Acta* 193-203 (1998).
Willumsen et al., "Enhanced hepatic fatty acid oxidation and upregulated carnitine palmitoyltransferase II gene expression by methyl 3-thiaoctadeca-6,9,12,15-tetraenoate in rats," 17 *J. Lipid Mediators Cell Signalling* 115-134 (1997).
Hill, A.J. & Fager, E.W., "Some α-Alkylthio Aliphatic Acids," *Journal of the American Chemical Society* (1943) 65(12):2300-2301.
Office Action dated Jul. 1, 2013, from U.S. Appl. No. 13/054,212.
Office Action dated Oct. 2, 2013, from U.S. Appl. No. 13/319,101.
Silverman, R.B., The Organic Chemistry of Drug Design and Drug Action, 1992, Academic Press, pp, 4, 14-28.
Shchepin, R. et al., "Auorum Sensing in *Candida albicans*: Probing Farnesol's Mode of Action with 40 Natural and Synthestic Farnesol Analogs," *Chemistry & Biology* (2003) 10:743-750.

\* cited by examiner

LIPID COMPOUNDS FOR USE IN COSMETIC PRODUCTS, AS FOOD SUPPLEMENT OR AS A MEDICAMENT

This is a national stage application under §371 of International Application No. PCT/NO2008/000391, filed Nov. 6, 2008, which claims priority to U.S. Provisional Application No. 60/986,698, filed Nov. 9, 2007, all of which are incorporated herein by reference in their entireties.

TECHNICAL FIELD

The present invention relates to lipid compounds of the general formula (I):

$$R_1-X-\underset{\underset{R_3}{|}}{\overset{\overset{R_2}{|}}{C}}-[CH_2]_n-OP_1 \qquad (I)$$

wherein

R$_1$ is selected from a C$_{10}$-C$_{21}$ alkyl, a C$_{10}$-C$_{21}$ alkenyl having 1-6 double bonds, and a C$_{10}$-C$_{21}$ alkynyl having 1-6 triple bonds;

R$_2$ and R$_3$ are the same or different and are selected from hydrogen and a C$_1$-C$_6$ alkyl group; and X is selected from O, S, SO, SO$_2$, Si or Se;

n=1 or 3; and

P$_1$ is selected from a hydrogen, a C$_{10}$-C$_{21}$ alkyl, a C$_{10}$-C$_{21}$ alkenyl having 1-6 double bonds, and a C$_{10}$-C$_{21}$ alkynyl having 1-6 triple bonds, optionally substituted; or P$_1$ is represented by:

(II)

(III)

wherein P$_2$, P$_3$ and P$_4$ are selected from a hydrogen, an alkyl, alkenyl, alkynyl, optionally substituted; or P$_1$ is a phosphonate or a phosphate ester, represented by (IV)

or P$_1$ is a sulphonate or a sulphate ester, represented by (V)

wherein P$_5$ is a hydrogen or a C$_1$-C$_6$ alkyl;

or a pharmaceutically acceptable salt, complex or solvate thereof.

The invention also relates to pharmaceutical compositions and lipid compositions comprising such compounds, and to such compounds for use as medicaments or for use in therapy, in particular for the treatment of diseases related to the cardiovascular, metabolic and inflammatory disease area.

BACKGROUND OF THE INVENTION

Up to date, there has been a lot of research on fatty acid analogues and their effects on diverse physiological processes impacting normal health and chronic diseases.

For example, dietary polyunsaturated fatty acids (PUFAs) have been shown to regulate plasma lipid levels, cardiovascular and immune functions, insulin action, and neuronal development and visual function.

Tetradecylthioacetic acid (TTA) is a modified fatty acid which has a number of powerful effects demonstrable both in vivo and in vitro on living organisms.

TTA has properties very similar to natural fatty acids, the main difference being that it cannot be oxidised by the mitochondrial β-oxidation, but significantly increases the oxidation of other fatty acids. Despite the fact that TTA is not able to undergo β-oxidation, it is metabolised in most ways as a normal saturated fatty acid.

TTA

TTA affects antioxidant status at different levels by having the potential of changing the antioxidant defense system in addition to being an antioxidant itself through its free radical scavenging capacity.

Addition of TTA may prevent the oxidative modification of LDL particles in plasma and reduce the generation of lipid peroxides.

SUMMARY OF THE INVENTION

One object of the present invention is to provide lipid compounds having pharmaceutical activity. This object is achieved by a lipid compound of formula (I)

$$R_1-X-\underset{\underset{R_3}{|}}{\overset{\overset{R_2}{|}}{C}}-[CH_2]_n-OP_1 \qquad (I)$$

wherein

R$_1$ is selected from a C$_{10}$-C$_{21}$ alkyl, a C$_{10}$-C$_{21}$ alkenyl having 1-6 double bonds, and a C$_{10}$-C$_{21}$ alkynyl having 1-6 triple bonds;

R$_2$ and R$_3$ are the same or different and are selected from hydrogen and a C$_1$-C$_6$ alkyl group; and X is selected from O, S, SO, SO$_2$, Si or Se;

n=1 or 3; and

P$_1$ is selected from a hydrogen, a C$_{10}$-C$_{21}$ alkyl, a C$_{10}$-C$_{21}$ alkenyl having 1-6 double bonds, and a C$_{10}$-C$_{21}$ alkynyl having 1-6 triple bonds, optionally substituted; or $P_1$ is represented by:

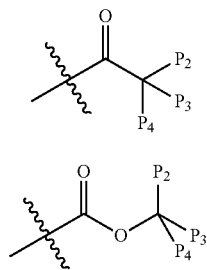

wherein $P_2$, $P_3$ and $P_4$ are selected from a hydrogen, an alkyl, alkenyl, alkynyl, which optionally may be substituted; or $P_1$ is a phosphonate or a phosphate ester, represented by

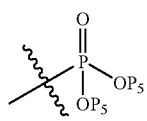

or $P_1$ is a sulphonate or a sulphate ester, represented by

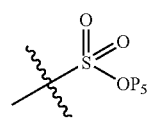

wherein $P_5$ is a hydrogen or a $C_1$-$C_6$ alkyl;
or a pharmaceutically acceptable salt, complex or solvate thereof.

In particular, the present invention relates to compounds of formula (I), wherein:

$R_1$ is a $C_{10}$-$C_{21}$ alkyl, e.g. a $C_{14}$ alkyl, and said lipid compound is derived from a saturated fatty acid.

$R_1$ is a $C_{10}$-$C_{22}$-alkenyl with 1-6 double bonds, wherein said lipid compound is either derived from a monounsaturated fatty acid or a polyunsaturated fatty acid.

When derived from a monounsaturated fatty acid, $R_1$ is typically a $C_{14}$-$C_{18}$ alkenyl, e.g. with 1-3 double bonds.

When derived from a polyunsaturated fatty acid, $R_1$ is typically a $C_{10}$-$C_{22}$ alkenyl with 3-6 double bonds, e.g. 3-6 methylene interrupted double bonds in Z configuration. For example, $R_1$ is:

- a $C_{15}$ alkenyl with 4 double bonds, e.g. a $C_{15}$ alkenyl with 4 methylene interrupted double bonds in Z-configuration
- a $C_{18}$ alkenyl with 3-5 double bonds, e.g. a $C_{18}$ alkenyl with 5 methylene interrupted double bonds in Z configuration
- a $C_{20}$ alkenyl with 5 methylene interrupted double bonds in Z-configuration
- a $C_{22}$ alkenyl with 6 methylene interrupted double bonds in Z-configuration Furthermore, $R_1$ may be a $C_{10}$-$C_{22}$ alkynyl, e.g. a $C_{16}$-$C_{22}$ alkynyl, wherein said lipid compound is derived from lipids comprising 1-6 triple bonds.

The present invention also relates to salts of the compounds according to formula (I). Such salts may comprise a monovalent cation such as $Li^+$, $Na^+$, $K^+$, $NH_4^+$, meglumine, tris(hydroxymethyl)aminomethane, diethylamine, arginine; a divalent ion such as $Mg^{2+}$, $Ca^{2+}$, ethylenediamine, piperazine; or a polyvalent cation such as chitosan.

In compounds of formula (I), wherein $P_1$ is represented by

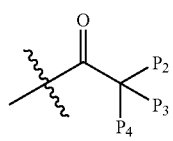

$P_2$, $P_3$, $P_4$ are typically selected from a hydrogen, a $C_1$-$C_6$ alkyl, e.g. methyl, ethyl, n-propyl, isopropyl, n-butyl, isobutyl, sec-butyl, n-hexyl, optionally substituted. Preferably one of $P_2$, $P_3$, $P_4$ is a hydrogen, a methyl group, or an isopropyl group. Typically, one of $P_2$, $P_3$, $P_4$ is a $C_1$-$C_6$ alkyl, e.g. methyl and the other two are represented by hydrogen. For example $P_1$ in formula (I) is represented by:

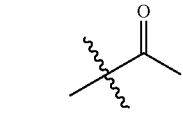

According to a preferred embodiment of the present invention, said alkyl, alkenyl or alkynyl is substituted with a carboxy group, typically a $C_1$-$C_6$ carboxy group. In this case, $P_1$ according to formula (II) may be represented by:

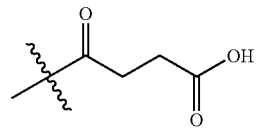

When $P_1$ is represented by formula (IIb) above, salts of the compounds according to formula (I) may be represented by

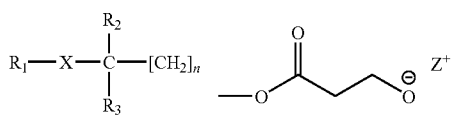

wherein $Z^+$ is selected from the group consisting of $Li^+$, $Na^+$, $K^+$, $NH_4^+$,

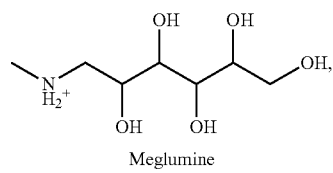

Meglumine

-continued

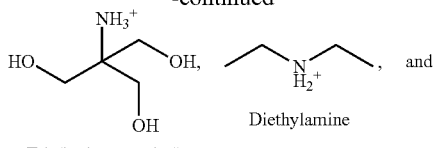
Tris(hydroxymethyl) aminomethane    Diethylamine

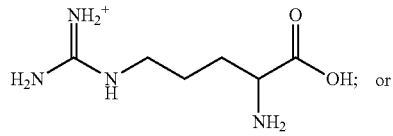
Arginine

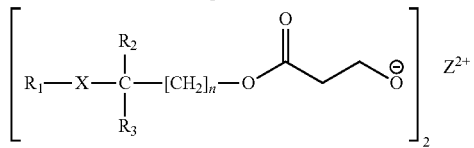

wherein $Z^{2+}$ is selected from the group consisting of $Mg^{2+}$, $Ca^{2+}$,

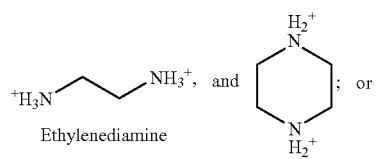
Ethylenediamine    Piperazine

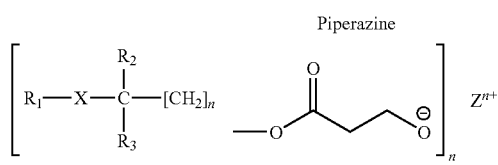

wherein $Z^{n+}$ is

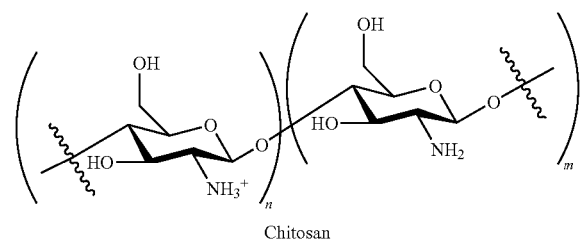
Chitosan

In formula (I), $P_1$ may also be represented by:

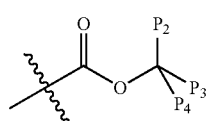
(III)

wherein $P_2$, $P_3$, $P_4$ is typically a hydrogen, a $C_1$-$C_6$ alkyl, e.g. methyl, ethyl, n-propyl, isopropyl, n-butyl, iso-butyl, sec-butyl or an n-hexyl. Preferably one of $P_2$, $P_3$, $P_4$ is a hydrogen, a methyl group or an isopropyl group.

When $P_1$ is a phosphonate or a phosphate ester represented by

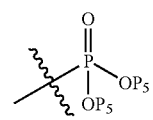
(IV)

$P_5$ is typically a hydrogen or a $C_1$-$C_6$ alkyl; preferably a hydrogen or a methyl group according to the formulas below

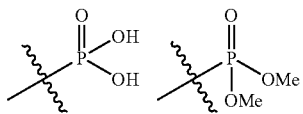 [SMILES: *P(=O)(O)O ; *P(=O)(OC)OC]

When $P_1$ is a sulphonate or a sulphate ester, represented by

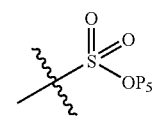
(V)

$P_5$ is typically a hydrogen or a $C_1$-$C_6$ alkyl, preferably a hydrogen or a methyl group according to the formulas below

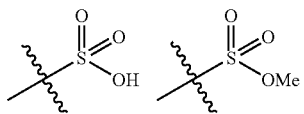 [SMILES: *S(=O)(=O)O ; *S(=O)(=O)OC]

In a preferred embodiment of the present invention, n is 1.

As mentioned, $R_2$ and $R_3$ may be the same or different and may be selected from a hydrogen and a $C_1$-$C_6$ alkyl group. Typically, $R_2$ and $R_3$ are both hydrogen.

Furthermore, in compounds of formula (I), X may be selected from O, S, SO, $SO_2$, Si and Se. Preferably, X is either S, Se or O. Typically it is S.

The compounds of formula (I) are capable of existing in stereoisomeric forms. It will be understood that the invention encompasses all optical isomers of the compounds of formula (I) and mixtures thereof, including racemates. Therefore, the present invention includes compounds of formula (I) that are racemic, either as the (S) or (R) enantiomer.

The present invention also relates to a lipid compound according of formula (I) for use as a medicament.

Cosmetic formulations comprising compounds of formula I form a further aspect of the invention.

In yet a further aspect, the present invention provides a food supplement, a food additive, or a neutraceutical preparation comprising a lipid compound of formula (I).

Such a food supplement may be produced for administration through any route of administration. For example, the food supplement may be administered as a liquid nutritional or as a beverage.

The food supplement may be in the form of a capsule, preferably a gelatine capsule, and the capsule may be flavoured.

In still a further aspect, the present invention provides a pharmaceutical composition comprising a compound of formula (I), preferably together with one or more pharmaceutically acceptable carriers or excipients.

The novel lipid compounds and compositions of the invention may be formulated in conventional administration forms, e.g. tablets, coated tablets, capsules, powders, granulates, solutions, dispersions, suspensions, syrups, emulsions, sprays, suppositories, pessaries, etc using conventional excipients, e.g. solvents, diluents, binders, sweeteners, aromas, pH modifiers, viscosity modifiers, antioxidants, corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances such as hard fat or suitable mixtures thereof etc. Conventional formulation techniques, well known in the art, may be used.

The compositions may likewise be administered by conventional administration routes, e.g. orally, by injection, infusion, nasally, rectally, etc. The use of orally administrable compositions, e.g. tablets, coated tablets, capsules, syrups, etc is especially preferred.

A suitable daily dosage of the compound according to formula (I) is 1 mg to 10 g of said compound; 50 mg to 1 g of said compound, or 50 mg to 200 mg of said compound.

The pharmaceutical composition according to the invention may be used as a medicament.

The present invention also relates to lipid composition comprising a lipid compound according to formula (I). Suitably, at least 60% by weight, or at least 80% by weight of the lipid composition is comprised of said compound.

The lipid composition may further comprise a pharmaceutically acceptable antioxidant, e.g. tocopherol.

Further, the present invention relates to a lipid composition for use as a medicament.

Additionally, the present invention relates to the use of a lipid compound according to formula (I) for the production of a medicament for:
the treatment and/or the prevention of peripheral insulin resistance and/or a diabetic condition
the reduction of plasma insulin, blood glucose and/or serum triglycerides.
the prevention and/or treatment of elevated triglyceride levels, LDL cholesterol levels, and/or VLDL cholesterol levels.
the prevention and/or treatment of a hyperlipidemic condition, e.g. hypertriglyceridemia
the treatment and/or prevention of type 2 diabetes
increasing serum HDL levels in humans
the treatment and/or the prevention of obesity or an over-weight condition
the reduction of body weight and/or for preventing body weight gain
the treatment and/or the prevention of a fatty liver disease, e.g. non-alcoholic fatty liver disease (NAFLD).
the treatment and/or the prevention of an inflammatory disease or condition, e.g. a chronic inflammatory disease like psoriasis
the treatment and/or the prevention of a condition selected from the group consisting of dyslipidemia, hypertension, atherosclerosis, cancer, rheumatoid arthritis, and brain disorders, e.g. MS and Alzheimer's The invention also relates lipid compounds according to formula (I) for the treatment of the above mentioned conditions, and to methods for the treatment and/or prevention of the conditions listed above, comprising administering to a mammal in need thereof a pharmaceutically active amount of a compound according to formula (I).

In addition, the present invention encompasses methods for manufacturing lipid compounds according to formula (I).

DETAILED DESCRIPTION OF THE INVENTION

The present inventors have found that specific pro-drugs of tetradecylthioacetic acid (TTA) or compounds that in vivo can be metabolized to TTA, in particular alcohols of these compounds and pro-drugs of the alcohol have remarkably good pharmaceutical activity. Such compounds are represented by formula (I).

As used herein, the term "lipid compound" relates to fatty acid analogues derived from e.g. monounsaturated fatty acids, polyunsaturated fatty acids and lipids comprising 1-6 triple bonds.

"Pro-drugs" are entities which may or may not possess pharmacological activity as such, but may be administered (such as orally or parenterally) and thereafter subjected to bioactivation (for example metabolization) in the body to form the agent of the present invention which is pharmacologically active.

A "pharmaceutically active amount" relates to an amount that will lead to the desired pharmacological and/or therapeutic effects, i.e. an amount of the combination product which is effective to achieve its intended purpose. While individual patient needs may vary, determination of optimal ranges for effective amounts of the combination product is within the skill of the art. Generally, the dosage regimen for treating a condition with the combination product of this invention is selected in accordance with a variety of factors, including the type, age, weight, sex, diet and medical condition of the patient.

By "a pharmaceutical composition" is meant a lipid compound according to the invention in any form suitable to be used for a medical purpose.

"Treatment" includes any therapeutic application that can benefit a human or non-human mammal. Both human and veterinary treatments are within the scope of the present invention. Treatment may be in respect of an existing condition or it may be prophylactic.

Nomenclature and Terminology:

Fatty acids are straight chain hydrocarbons possessing a carboxyl (COOH) group at one end (α) and (usually) a methyl group at the other (ω) end. In chemistry, the numbering of the carbon atoms starts from the α end.

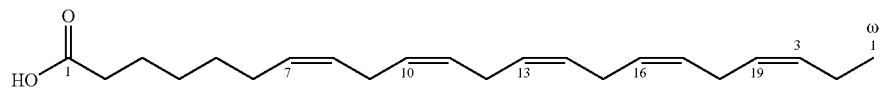

The α carbon refers to the first carbon after the carbon that attaches to the functional group, and the second carbon is the β carbon.

As used herein, the expression "methylene interrupted double bonds" relates to the case when a methylene group is located between to separate double bonds in a carbon chain of a lipid compound.

The basic idea of the present invention is a lipid compound of formula (I):

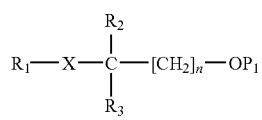
(I)

wherein $R_1$, $R_2$, $R_3$, X, n, and $P_1$ are as defined above.

The resulting compound is a lipid compound with a heteroatom incorporated in the lipid chain, i.e. a lipid compound with a heteroatom preferably in the β-position.

More particularly, the present inventors have surprisingly found that the following lipid compound categories A-D are particularly preferable.

Category A
derived from saturated fatty acids
$R_1$ is a $C_{10}$-$C_{21}$ alkyl

Example 1

$R_1 = C_{14}$, n=1

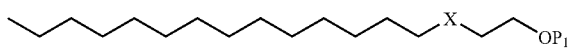

Category B
derived from monounsaturated fatty acids
$R_1$ is a $C_{10}$-$C_{21}$ alkenyl having 1 double bond

Example 2

$R_1 = C_{18}$, n=1

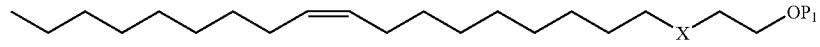

Example 3

$R_1 = C_{14}$, n=1, X=S

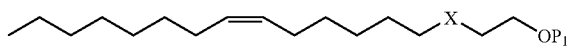

Category C
derived from polyunsaturated fatty acids
$R_1$ is a $C_{10}$-$C_{22}$ alkenyl having 1-6 double bonds

Example 4

$R_1 = C_{20}$ with 5 methylene interrupted double bonds in Z-configuration, n=1, X=S

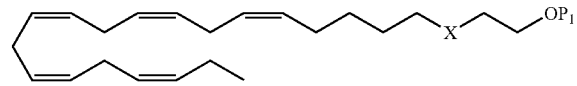

Example 5

$R_1 = C_{22}$ with 6 methylene interrupted double bonds in Z-configuration, n=1

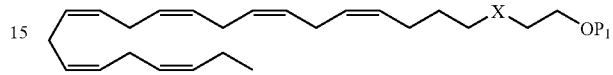

Example 6

$R_1 = C_{18}$ with 3 methylene interrupted double bonds in Z-configuration, n=1

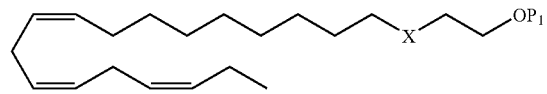

Example 7

$R_1 = C_{15}$ with 4 methylene interrupted double bonds in Z-configuration, n=1

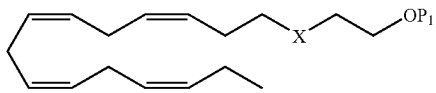

Example 8

$R_1 = C_{15}$ with 4 double bonds, n=1

Example 9

$R_1$ is $C_{18}$ with 5 double bonds methylene interrupted double bonds in Z-configuration, n=1

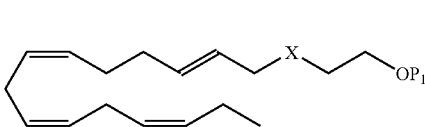

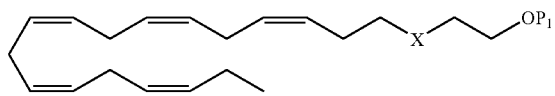

Example 10

R$_1$=C$_{18}$ with 5 double bonds, n=1

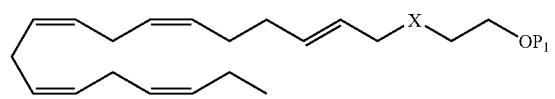

Category D
    derived from lipids containing 1-6 triple bonds

Example 11

R$_1$=C$_{18}$ with 1 triple bond, n=1

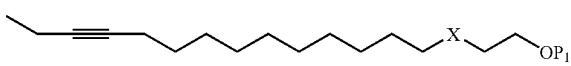

The present invention will now be further described by the following non-limiting examples.
General Synthesis for Compounds Wherein X is Sulphur and n=1

The compounds of general formula (I) can be prepared by the following general procedures:

Method 1:

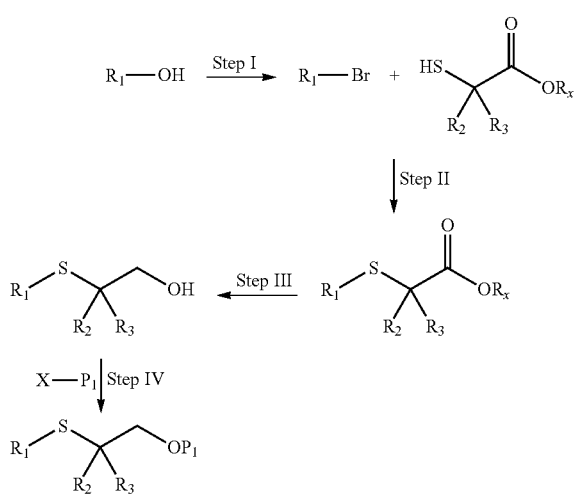

Method II:

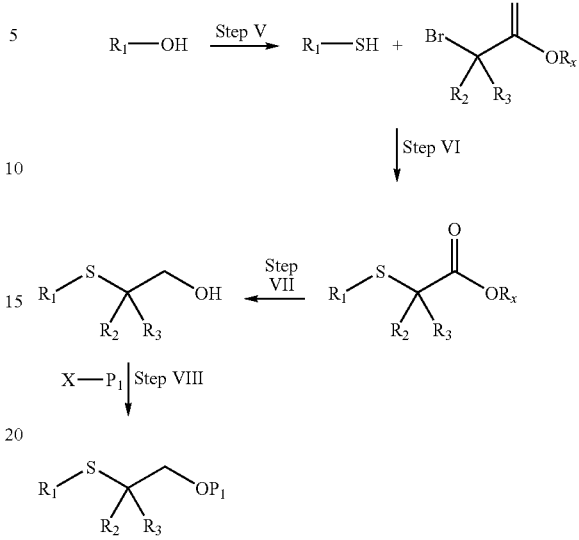

The unsaturated alcohols may be prepared directly from the carboxylic esters of the naturally occurring unsaturated fatty acids; alpha-linolenic acid, oleic acid, conjugated linoleic acid, linoleic acid, eicosapentaenoic acid, etc. by reduction with diisobutylaluminiumhydride. The alcohols can also be prepared by degradation of the polyunsaturated fatty acids EPA and DHA as described by Holmeide et al. (*J. Chem. Soc., Perkin Trans.* 1, 2000, 2271). In this case one can start with purified EPA or DHA, but it is also possible to start with fish oil containing EPA and DHA in mixture.

The saturated alcohols can be obtained from their corresponding carboxylic acids or carboxylic esters.

Examples 1 to 4

In the following examples the structures were verified by NMR. The NMR spectra were recorded in CDCl$_3$. J values are given in Hz.

The following lipid derivatives have been prepared and characterised, and thus in accordance with the present invention there is provided compounds of the formula (I)

Preparation and characterisation of specific fatty acid derivatives of formula (I)

Example 1

2-Tetradecylsulfanyl-ethanol

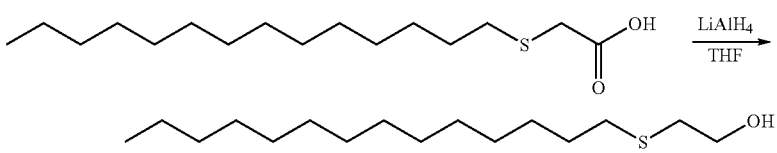

A solution of tetradecylsulfanyl-acetic acid (1.50 g, 520 mmol) in dry THF (10 ml) was added drop wise to a suspension of LiAlH₄ (0.40 g, 10.4 mmol) in dry THF (30 ml) at 0° C. The mixture was stirred at 0° C. for one hour and then at ambient temperature for 18 hours. Saturated NH₄Cl (40 ml) was added, and the resulting mixture was filtered through a short pad of celite. The phases were separated and the aqueous layer was extracted with diethyl ether (50 ml). The combined organic phases was washed with brine (50 ml), dried (Na₂SO₄) and concentrated in vacuo. Purification by flash chromatography on silica gel (heptane:EtOAc 4:1) afforded 0.76 g (54%) of the title compound as a colourless solid.

¹H-NMR (200 MHz, CDCl₃): δ 0.85 (t, 3H), 1.23-1.49 (m, 22H), 1.55 (m, 2H), 2.48 (t, 2H), 2.69 (t, 2H), 3.68 (t, 2H)
MS (ESI): 297 [M+Na⁺]⁺.

Example 2

(2-tetradecylsulfanyl-ethyl)acetate

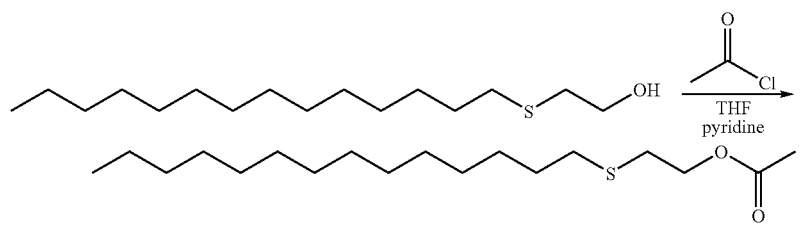 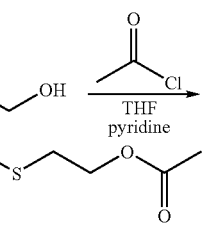

2-Tetradecylsulfanyl-ethanol (0.54 g, 1.97 mmol) was dissolved in dry THF (10 ml) and pyridine (0.16 ml, 1.97 mmol) was added followed by acetyl chloride (0.15 m, 2.16 mmol). The resulting mixture was allowed to stir at ambient temperature for 23 hours, then another portion of acetyl chloride (0.075 ml, 1.08 mmol) and pyridine (0.080 ml, 0.95 mmol) was added. The mixture was stirred at ambient temperature for a further 90 minutes and then portioned between diethyl ether (30 ml) and 10% NH₄Cl (30 ml). The organic layer was washed with brine (40 ml), dried (Na₂SO₄) and concentrated in vacuo. Toluene (10 mL) was added to the residue. The solvents were evaporated in vacuo and the crude product was purified by flash chromatography on silica gel (heptane:EtOAc 9:1) to afford 0.45 g (72%) of the title compound as a colorless solid.

¹H-NMR (200 MHz, CDCl₃): δ 0.85 (t, 3H), 1.23-1.49 (m, 22H), 1.49-1.60 (m, 2H), 2.04 (s, 3H), 2.53 (t, 2H), 2.71 (t, 2H), 4.19 (t, 2H);
MS (ESI): 317 [M+H⁺]⁺, 339 [M+Na⁺]⁺.

Example 3

(5E,9Z,12Z,15Z,18Z)-3-thia-heneicosa-pentaen-1-ol

Step 1: Ethyl (5E,9Z,12Z,15Z,18Z)-3-thia-heneicosa-pentaenoate

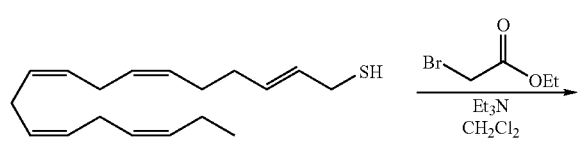 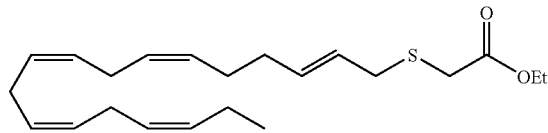

Et₃N (0.28 ml, 2.07 mmol) followed by bromo ethylacetate (0.22 ml, 1.97 mmol) were added to a mixture of (2E,6Z,9Z,12Z,15Z)-octadecapentaene-1-thiol (0.52 g, 1.88 mmol) in dry CH₂Cl₂ (10 ml) under an inert atmosphere. The resulting solution was stirred at ambient temperature for 18 hours. CH₂Cl₂ (20 ml) was added. The resulting mixture was washed with water (20 ml) and brine (30 ml), dried (Na₂SO₄) and concentrated in vacuo. The residue was purified by flash chromatography on a short silica column (heptane:EtOAc 99:1 then 95:5) to afford 0.54 g (79%) of the title compound as a colorless oil.

¹H-NMR (200 MHz, CDCl₃): δ 0.95 (t, 3H), 1.27 (t, 3H), 1.98-2.19 (m, 6H), 2.76-2.90 (m, 6H), 3.13 (s, 2H), 3.18 (d, 2H), 4.16 (q, 2H), 5.22-5.50 (m, 9H), 5.53-5.71 (m, 1H);
MS (ESI): 385 [M+Na⁺]⁺.

Step 2:
(5E,9Z,12Z,15Z,18Z)-3-thia-heneicosa-pentaen-1-ol

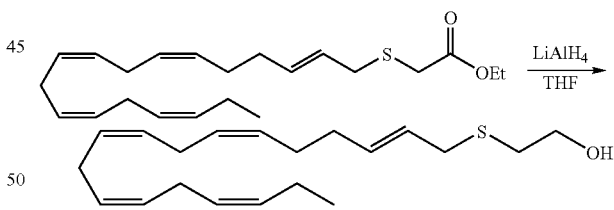

A solution of ethyl (5E,9Z,12Z,15Z,18Z)-3-thia-heneicosa-pentaenoate (0.54 g, 1.49 mmol) in dry THF (5 ml) was added drop wise to a stirred suspension of LiAlH₄ (0.062 g, 1.64 mmol) in dry THF (10 ml) at 0° C. under inert atmosphere. The resulting solution was stirred at 0° C. for 15 minutes. 10% NH₄Cl (20 ml) was added drop wise and the resulting mixture was filtered through a short pad of celite. The celite pad was washed with water (20 ml) and diethyl ether (20 ml) and the phases were separated. The aqueous phase was extracted with diethyl ether (2×20 ml). The combined organic extracts were washed with brine (20 ml), dried (Na₂SO₄) and concentrated in vacuo. The residue was purified by flash chromatography on silica gel (heptane:EtOAc 4:1). This afforded 0.39 g (81%) of the title compound as a colorless oil.

¹H-NMR (200 MHz, CDCl₃): δ 0.96 (t, 3H), 1.98-2.12 (m, 7H), 2.66 (t, 2H), 2.76-2.85 (m, 6H), 3.08 (d, 2H), 3.67 (q, 2H), 5.26-5.56 (m, 10H);
MS (ESI): 343 [M+Na⁺]⁺.

Example 4

(all-Z)-2-ethyl-3-thia-tricosa-8,11,14,17,20-pentaen-1-ol

Step 1: (all-Z)-eicosa-5,8,11,14,17-pentaen-1-yl thioacetate

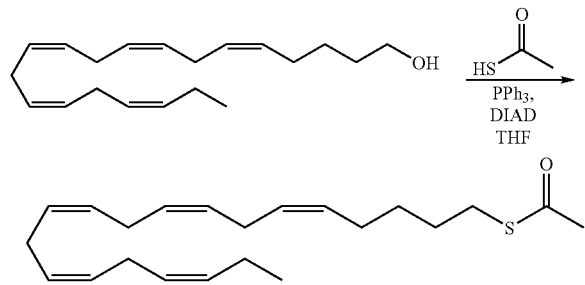

Triphenylphosphine, PPh₃ (79.11 g, 302 mmol) was dissolved in dry THF (600 ml) at 0° C. under inert atmosphere and added DIAD (59.06 ml, 305 mmol) dropwise. After 40 minutes at 0° C. a solution of (all-Z)-5,8,11,14,17-eicosapentaen-1-ol (43.50 g, 151 mmol) and thioacetic acid (21.56 ml, 302 mmol) in dry THF (400 mL) was added dropwise. The resulting turbid mixture was stirred at 0° C. for 40 minutes, followed by ambient temperature for 1.5 h. Heptane (600 ml) was added, the mixture was stirred for ten minutes and the precipitated white solid removed by filtration. This procedure was repeated twice and finally the residue after concentration was stirred in heptane (400 ml) for 24 h. Filtration and purification of the residue by flash chromatography (SiO₂, EtOAc:Heptane 2:98) provided 46.6 g (89%) of the title compound as a colourless oil.

¹H-NMR (200 MHz, CDCl₃); δ 0.95 (t, 3H), 1.41-1.63 (m, 4H), 2.05 (m, 4H), 2.30 (s, 3H), 2.76-2.89 (m, 10H), 5.22-5.44 (m, 10H)
MS (ESI): 369 [M+Na⁺]⁺.

Step 2: (all Z)-eicosa-5,8,11,14,17-pentaene-1-thiol

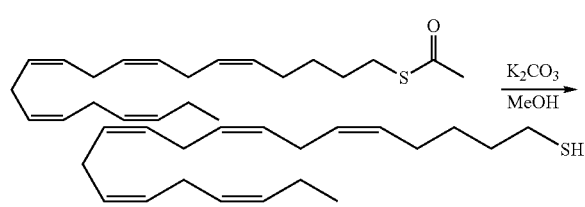

K₂CO₃ (18.6 g, 134 mmol) was added to a solution of (all-Z)-eicosa-5,8,11,14,17-pentaen-1-yl thioacetate (46.6 g, 134 mmol) in dry MeOH (500 ml) under inert atmosphere. The mixture was stirred at ambient temperature for 1.5 h. 1M HCl (350 m), water (350 m) and diethyl ether (500 ml) was added. The phases were separated and the aqueous phase was extracted with diethyl ether (500 ml). The combined organic extracts were washed with brine (250 m), dried (Na₂SO₄), filtered and concentrated in vacuo. Purification by flash chromatography (SiO₂, 1%-2%-3% EtOAc in heptane) afforded 30.0 g (75%) of the title compound as a pale yellow oil.

¹H-NMR (200 MHz, CDCl₃): δ 0.95 (t, 3H), 1.35-1.61 (m, 4H), 2.06 (m, 4H), 2.51 (m, 2H), 2.76-2.85 (m, 8H), 5.23-5.44 (m, 10H).

Step 3: (all-Z)-2-ethyl-3-thia-tricosa-8,11,14,17,20-pentaenoic acid

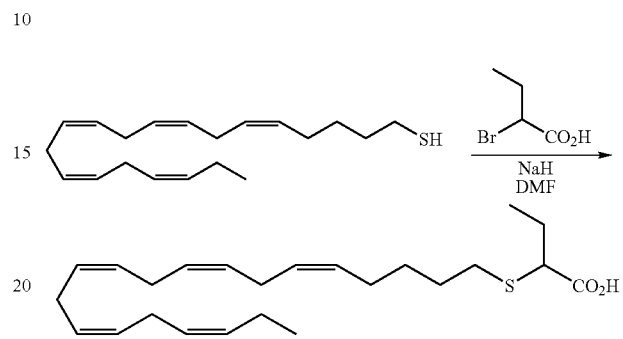

A solution of (all Z)-eicosa-5,8,11,14,17-pentaene-1-thiol (20.0 g, 65.7 mmol) in dry DMF (150 m) at 0° C. under inert atmosphere was added NaH (2.84 g, 72.2 mmol). The resulting yellow suspension was stirred at 0° C. for 30 min and then added to a pre made mixture of 2-bromo butyric acid (7.73 ml, 72.2 mmol) and NaH (3.15 g, 78.8 mmol) in DMF (150 m) at 0° C. The resulting clear solution was stirred at ambient temperature under inert atmosphere for 3 h, and then poured into cold saturated NH₄Cl (300 ml). 1M HCl was added until pH=1 and the resulting mixture was extracted twice with diethyl ether (400 ml each). The combined organic extracts were washed with brine (250 ml), dried (MgSO₄), filtered and concentrated in vacuo to afford 28 g of crude product. The crude product was first filtered through a short pad of silica gel (heptane: EtOAc (with 5% HCOOH) 95:5-90:10) to afford 11.5 g of impure product. A second purification by ordinary flash chromatography (SiO₂, heptane: EtOAc (with 5% HCOOH) 9:1-8:2-7:3) afforded 10.15 g (40%) of the title compound as a pale yellow oil.

¹H-NMR (300 MHz, CDCl₃): δ 0.97 (t, 3H), 1.07 (t, 3H), 1.46 (m, 2H), 1.64-1.74 (m, 3H), 1.79 (m, 1H), 2.10 (m, 4H), 2.66 (m, 2H), 2.83 (m, 8H), 3.20 (t, 1H), 5.35-5.42 (m, 10H)
MS (ESI): 389 [M–H⁺]⁻.

Step 4: (all-Z)-2-ethyl-3-thia-tricosa-8,11,14,17,20-pentaen-1-ol

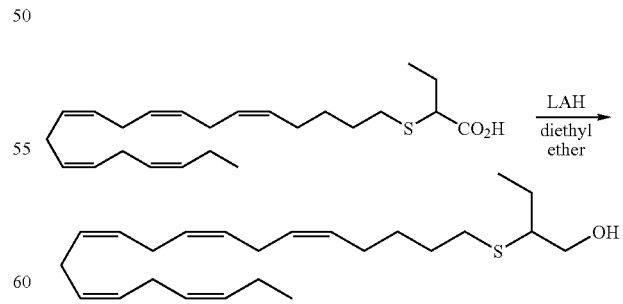

(all-Z)-2-ethyl-3-thia-tricosa-8,11,14,17,20-pentaenoic acid (100 mg, 0.26 mmol) was dissolved in dry THF (1 ml) and added drop wise to a solution of lithium aluminium hydride (19 mg, 0.51 mmol) in dry THF (4 m) at 0° C. The resulting turbid mixture was stirred at 0° C. for 30 min, and then carefully added saturated NH₄Cl (15 ml). The resulting mixture was extracted twice with heptane (15 ml each). The combined organic extracts were dried ($Na_2SO_4$), filtered and purified by flash chromatography ($SiO_2$, heptane: EtOAc 95:5-90:10) to afford 70 mg (71%) of the title compound.

$^1$H-NMR (300 MHz, $CDCl_3$): δ 0.95 (t, 3H), 1.05 (t, 3H), 1.40-1-70 (m, 6H), 2.10 (m, 4H), 2.30 (m, 1H), 2.50 (m, 2H), 2.65-2.75 (m, 1H), 2.75-2.90 (m, 8H), 3.50 (m, 1H), 3.65 (m, 1H), 5.25-5.50 (m, 10H)

$^{13}$C-NMR (75 MHz, $CDCl_3$): δ 12.12, 14.66, 20.95, 25.22, 26.03 (3 signals), 27.17, 29.24, 30.02. 30.45. 51.76, 63.86, 127.40, 128.26, 128.43, 128.50, 128.56, 128.94, 130.04, 132.41 (three signals hidden)

MS (ESI): 399 $[M+Na^+]^+$.

The invention shall not be limited the shown embodiments and examples.

The invention claimed is:

1. A lipid compound of formula (I):

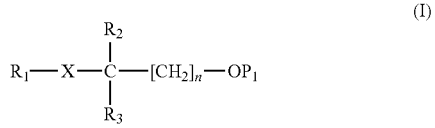

(I)

wherein
  $R_1$ is chosen from a $C_{10}$-$C_{22}$ alkenyl having 1-6 double bonds and a $C_{10}$-$C_{21}$ alkynyl having 1-6 triple bonds;
  $R_2$ and $R_3$ are the same or different and are chosen from hydrogen and a $C_1$-$C_6$ alkyl group with the proviso that $R_2$ and $R_3$ cannot both be hydrogen; and X is chosen from O, S, SO, or $SO_2$;
  n is 1 or 3; and
  $P_1$ is chosen from
    hydrogen; a $C_{10}$-$C_{21}$ alkyl, a $C_{10}$-$C_{21}$ alkenyl having 1-6 double bonds, and a $C_{10}$-$C_{21}$ alkynyl having 1-6 triple bonds, optionally substituted;
    a group of formula (II) or formula (III):

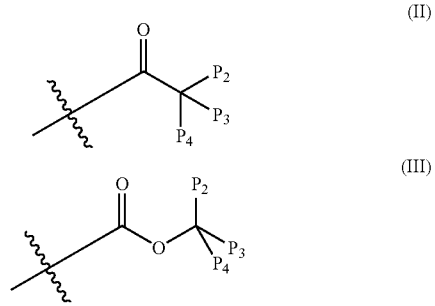

(II)

(III)

wherein $P_2$, $P_3$, and $P_4$ are chosen from hydrogen, an alkyl, an alkenyl, an alkynyl, optionally substituted; and
  a phosphonate or a phosphate ester of formula (IV) or a sulphonate or a sulphate ester of formula (V):

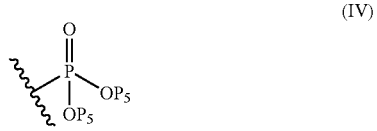

(IV)

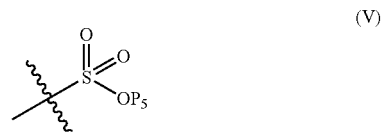

(V)

wherein $P_5$ is chosen from hydrogen and a $C_1$-$C_6$ alkyl;
or a pharmaceutically acceptable salt thereof.

2. The lipid compound according to claim 1, wherein $R_1$ is a $C_{10}$-$C_{22}$-alkenyl with 1-6 double bonds.

3. The lipid compound according to claim 2, wherein the lipid compound is derived from a monounsaturated fatty acid.

4. The lipid compound according to claim 2, wherein the lipid compound is derived from a polyunsaturated fatty acid.

5. The lipid compound according to claim 2, wherein $R_1$ is a $C_{10}$-$C_{22}$ alkenyl with 3-6 double bonds.

6. The lipid compound according to claim 5, wherein $R_1$ is a $C_{10}$-$C_{22}$ alkenyl with 3-6 methylene interrupted double bonds in Z configuration.

7. The lipid compound according to claim 1, wherein $R_1$ is a $C_{10}$-$C_{22}$ alkynyl, and wherein the lipid compound is derived from lipids comprising 1-6 triple bonds.

8. The lipid compound according to claim 1, wherein the salt of the lipid compound comprises at least one of a monovalent cation chosen from $Li^+$, $Na^+$, $NH_4^+$, meglumine, tris (hydroxymethyl)aminomethane, diethylamine, arginine; a divalent ion chosen from $Mg^{2+}$, $Ca^{2+}$, ethylenediamine, piperazine; and a polyvalent cation chosen from chitosan.

9. The lipid compound according to claim 1, wherein when $P_1$ is chosen from a $C_{10}$-$C_{21}$ alkyl, a $C_{10}$-$C_{21}$ alkenyl having 1-6 double bonds, and a $C_{10}$-$C_{21}$ alkynyl having 1-6 triple bonds, at least one of the alkyl, alkenyl, and alkynyl is substituted with a carboxy group.

10. The lipid compound according to claim 1, wherein $P_1$ is a group of formula (II):

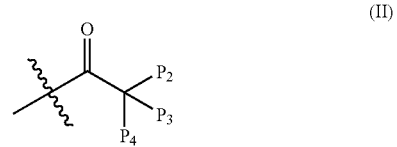

(II)

wherein $P_2$, $P_3$, and $P_4$ are chosen from hydrogen and a $C_1$-$C_6$ alkyl, optionally substituted.

11. The lipid compound according to claim 10, wherein $P_2$, $P_3$, and $P_4$ are chosen from hydrogen, methyl, and isopropyl.

12. The lipid compound according to claim 10, wherein one of $P_2$, $P_3$, and $P_4$ is a methyl group, and the other two are hydrogen.

13. The lipid compound according to claim 1, wherein $P_1$ is a group of formula (III):

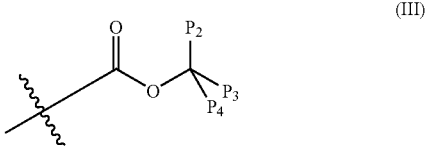

(III)

wherein $P_2$, $P_3$, and $P_4$ are chosen from hydrogen and a $C_1$-$C_6$ alkyl.

14. The lipid compound according to claim 13, wherein $P_2$, $P_3$, and $P_4$ are chosen from hydrogen, methyl, and isopropyl.

15. The lipid compound according to claim 1, wherein $P_1$ is a group of formula (IV):

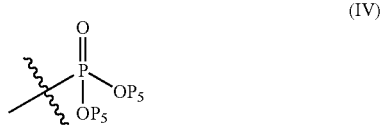

(IV)

wherein $P_5$ is chosen from hydrogen and a methyl group.

16. The lipid compound according to claim 1, wherein $P_1$ is a group of formula (V):

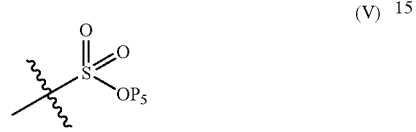

(V)

wherein $P_5$ is chosen from hydrogen and a methyl group.

17. The lipid compound according to claim 1, wherein n is 1.

18. The lipid compound according to claim 1, wherein X is S.

19. The lipid compound according to claim 1, wherein X is O.

20. A food supplement composition comprising a lipid compound according to claim 1.

21. A pharmaceutical composition comprising a lipid compound according to claim 1.

22. The composition according to claim 21, further comprising a pharmaceutically acceptable carrier, excipient, diluent, or any combination thereof.

23. The composition according to claim 21 formulated for oral administration.

24. The composition according to claim 23, wherein the composition is in the form of a capsule or a sachet.

25. The composition according to claim 21, wherein the composition is formulated to provide a daily dosage ranging from 1 mg to 10 g of the lipid compound.

26. The composition according to claim 25, wherein the daily dosage ranges from 50 mg to 1 g of the lipid compound.

27. The composition according to claim 26, wherein the daily dosage ranges from 50 mg to 200 mg of the lipid compound.

28. A lipid composition comprising a lipid compound according to claim 1.

29. The composition according to claim 28, wherein the lipid composition comprises at least 60% by weight of the lipid compound.

30. The composition according to claim 29, wherein the lipid composition comprises at least 80% by weight of the lipid compound.

31. The composition according to claim 28, further comprising a pharmaceutically acceptable antioxidant.

32. The composition according to claim 31, wherein the antioxidant is tocopherol.

33. A method for treating at least one condition chosen from peripheral insulin resistance and a diabetic condition, comprising administering to a mammal in need thereof a pharmaceutically-active amount of a lipid compound according to claim 1.

34. A method for reducing at least one of plasma insulin, blood glucose, and serum triglycerides, comprising administering to a mammal in need thereof a pharmaceutically-active amount of a lipid compound according to claim 1.

35. A method for treating at least one of elevated triglyceride levels, LDL cholesterol levels, and VLDL cholesterol levels, comprising administering to a mammal in need thereof a pharmaceutically-active amount of a lipid compound according to claim 1.

36. A method for preventing or treating a hyperlipidemic condition, comprising administering to a mammal in need thereof a pharmaceutically-active amount of a lipid compound according to claim 1.

37. A lipid compound of formula (I), wherein said compound is

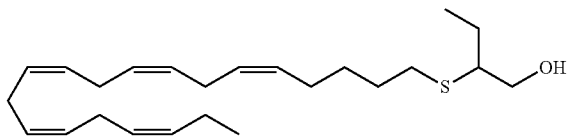 [SMILES: CC/C=C\C/C=C\C/C=C\C/C=C\C/C=C\CCCCSC(CC)CO]

(all-Z)-2-ethyl-3-thia-tricosa-8,11,14,17,20-pentaen-1-ol.

38. A method for the preparation of a compound of formula (I), wherein said compound is

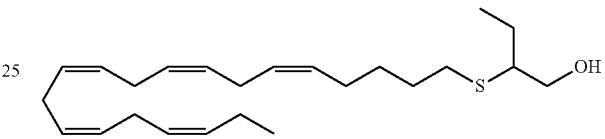

(all-Z)-2-ethyl-3-thia-tricosa-8,11,14,17,20-pentaen-1-ol, comprising:
  a) reacting (all-Z)-5,8,11,14,17-eicosapentaen-1-ol with thioacetic acid to form (all-Z)-eicosa-5,8,11,14,17-pentaen-1-ylthioacetate;
  b) converting (all-Z)-eicosa-5,8,11,14,17-pentaen-1-ylthioacetate into (all-Z)-eicosa-5,8,11,14,17-pentaene-1-thiol;
  c) converting (all-Z)-eicosa-5,8,11,14,17-pentaene-1-thiol into (all-Z)-2-ethyl-3-thia-tricosa-8,11,14,17,20-pentaenoic acid;
  d) reducing (all-Z)-2-ethyl-3-thia-tricosa-8,11,14,17,20-pentaenoic acid to (all-Z)-2-ethyl-3-thia-tricosa-8,11,14,17,20-pentaen-1-ol with a reducing agent; and
  e) isolating said (all-Z)-2-ethyl-3-thia-tricosa-8,11,14,17,20-pentaen-1-ol.

39. The method according to claim 38, wherein step a) is conducted under standard Mitsunobu conditions.

40. The method according to step 38, wherein step b) is conducted under basic conditions.

41. The method according to claim 40, wherein the base is $K_2CO_3$.

42. The method according to claim 38, wherein the reducing agent is lithium aluminum hydride.

43. A method for the preparation of a lipid compound according to claim 1, when X is S comprising:
  a) converting $R_1$—OH into a thiol, which is $R_1$—SH;
  b) reacting $R_1$—SH that results from step a) with

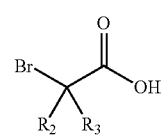

to form

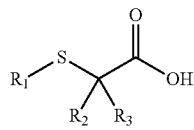

under basic conditions;
  c) reducing the thioether that results from step b), which is

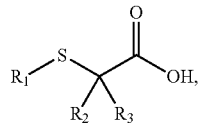

with a reducing agent to form

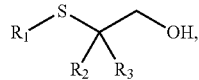

wherein
  $R_1$, $R_2$, and $R_3$ are as defined in claim 1.

44. The method according to claim 43, wherein the reducing agent in step c) is lithium aluminum hydride.

45. The method according to claim 43, wherein the base in step b) is a $K_2CO_3$.

46. A method for the preparation of a lipid compound according to claim 1, when X is S comprising:

a) converting $R_1$—OH into $R_1$—Br;
b) reacting $R_1$—Br that results from step a) with

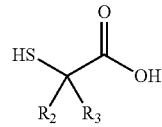

to form

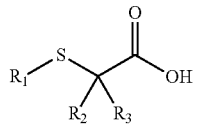

under basic conditions;
  c) reducing the thioether that results from step b), which is

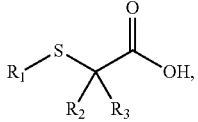

with a reducing agent to form

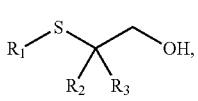

wherein
  $R_1$, $R_2$, and $R_3$ are as defined in claim 1.

47. The method according to claim 46, wherein the reducing agent in step c) is lithium aluminum hydride.

48. The method according to claim 46, wherein the base in step b) is a $K_2CO_3$.

* * * * *

UNITED STATES PATENT AND TRADEMARK OFFICE
CERTIFICATE OF CORRECTION

PATENT NO. : 8,741,966 B2  
APPLICATION NO. : 12/741890  
DATED : June 3, 2014  
INVENTOR(S) : Holmeide Page 1 of 1

It is certified that error appears in the above-identified patent and that said Letters Patent is hereby corrected as shown below:

In the Claims

Claim 38, column 20, line 33,
"17-pentaen-1-ylthioacetate" should read --17-pentaen-1-yl thioacetate--.

Claim 38, column 20, lines 34-35,
"17-pentaen-1-ylthioacetate" should read --17-pentaen-1-yl thioacetate--.

Claim 43, column 20, line 57, "claim 1, when X is S comprising:" should read --claim 1, when X is S, comprising:--.

Claim 46, column 21, line 36, "claim 1, when X is S comprising:" should read --claim 1, when X is S, comprising:--.

Signed and Sealed this
Twelfth Day of August, 2014

Michelle K. Lee
*Deputy Director of the United States Patent and Trademark Office*